(12) United States Patent
Westerterp et al.

(10) Patent No.: US 6,810,349 B2
(45) Date of Patent: Oct. 26, 2004

(54) SYSTEM AND METHOD FOR DETERMINING A MEASURE OF THE PHYSICAL ACTIVITY OF AN OBJECT

(75) Inventors: Klaas Roelof Westerterp, Maastricht (NL); Annelis Heleen Carolien Goris, Eindhoven (NL); Johannes Johanna Van Herk, Eindhoven (NL); Frits Tobi De Jongh, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 9 days.

(21) Appl. No.: 10/266,272

(22) Filed: Oct. 8, 2002

(65) Prior Publication Data

US 2003/0074157 A1 Apr. 17, 2003

(30) Foreign Application Priority Data

Oct. 11, 2001 (EP) .............................................. 01203856

(51) Int. Cl.$^7$ ................................................ G01D 1/00
(52) U.S. Cl. .................................... 702/127; 600/300
(58) Field of Search ........................... 702/127; 600/300

(56) References Cited

U.S. PATENT DOCUMENTS

| | | | | |
|---|---|---|---|---|
| 4,611,491 A | * | 9/1986 | Brown et al. ............. | 73/514.21 |
| 5,408,878 A | * | 4/1995 | Lysen ....................... | 73/514.34 |
| 5,788,655 A | * | 8/1998 | Yoshimura et al. ......... | 600/587 |
| 6,002,963 A | * | 12/1999 | Mouchawar et al. .......... | 607/18 |
| 6,095,949 A | * | 8/2000 | Arai .............................. | 482/4 |
| 6,513,532 B2 | * | 2/2003 | Mault et al. ................. | 600/595 |
| 6,595,929 B2 | * | 7/2003 | Stivoric et al. ............. | 600/549 |
| 6,605,038 B1 | * | 8/2003 | Teller et al. ................ | 600/300 |

OTHER PUBLICATIONS

"Seismic Accelerometer" from Instrumentation and Measurement Technology Conference, 1999, IMTC/99, Proceedings of the 16th IEEE, vol.: 3, May 24–26, 1999 pp. 1342–1346 vol. 3 by Garcia et al.*

"Method to Assess Physical Activity with Special Reference to Motion Sensors and Accelerometers" from IEEE Transactions on Biomedical Engineering vol. 38, No. 3, Mar. 1991 by Meijer et al.*

Bouten Carlijn et al; "Daily Physical Activity Assessment: Comparison Between Movement Registration and Doubly Labeled Water", Journal of Applied Physiology, vol. 81, No. 2, Aug. 1996, pp. 1019–1026, XP008017612.

Benefice Eric et al; "Assessment F Physical Activity Among Rural Senegalese Adolecent Girls: Influence of Age, Sexual Maturation, and Body Composition", Journal of Adolescent Health, vol. 28, No. 4, 2001, pp. 319–327, XP002242564.

"A Triaxial Accelerometer and Portable Data Processing Unit for the Assessment of Daily Physical Activity", by Bouten et al., IEEE Transaction on Biomedical Engineering, vol. 44, No. 3, Mar. 1997.

* cited by examiner

*Primary Examiner*—John Barlow
*Assistant Examiner*—Anthony T. Dougherty

(57) ABSTRACT

The invention concerns a system and a method for calculating the physical activity level (PAL) as an objective measure of the physical activity of an object over a certain period of time. The system (1) comprises an activity monitor (2) having three orthogonally mounted accelerometers (4, 5 and 6) for measuring the acceleration of the object, data processing means (7) and memory means (8). The activity monitor (2) further comprises communication means (12) for communicating with calculating means (3) for calculating the PAL. According to the claimed method the calculating means use the following algorithm:

Figure 1:
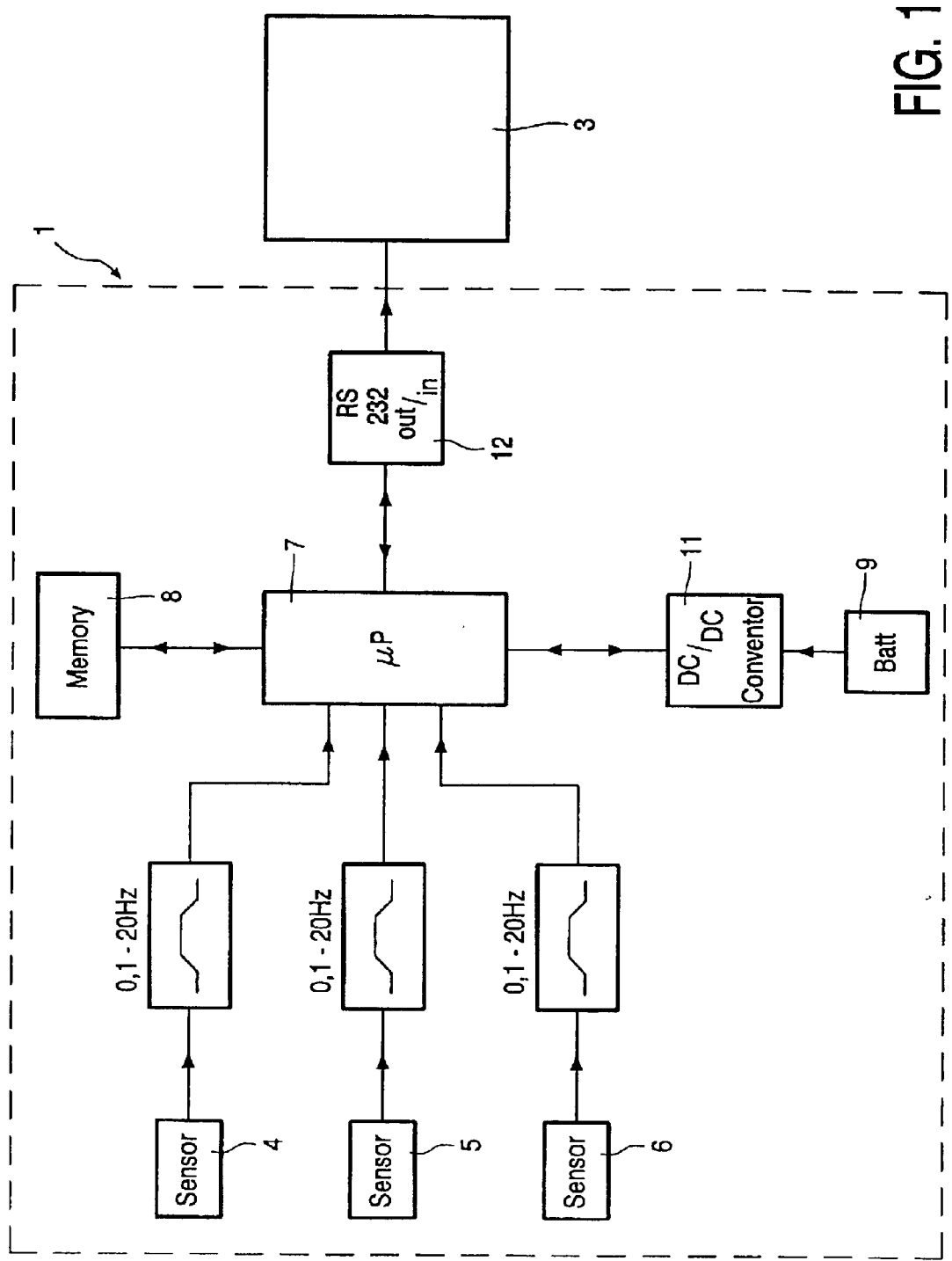

$$PAL = \text{factor } 1 + \text{factor } 2 * (\text{variable } 1)^{\text{factor } 3} + \text{factor } 4 * (\text{variable } 2)^{\text{factor } 5} + \ldots + \text{factor}(2n) * (\text{variable } n)^{\text{factor } (2n+1)}.$$

Herein are variable 1 through variable n related to the object and/or the system and are factor 1 through factor 2n+1 to be determined by validation of the system.

19 Claims, 2 Drawing Sheets

SYSTEM AND METHOD FOR DETERMINING A MEASURE OF THE PHYSICAL ACTIVITY OF AN OBJECT

The present invention relates to a system for determining a measure of the physical activity of an object over a certain period of time, said system comprising measurement means for measuring data relating to movement of the object, data processing means for processing the measured data and memory means for storing the processed data. The present invention also relates to a method for determining a measure of the physical activity of an object over a certain period of time comprising the steps of:

a) measuring data relating to movement of the object;
b) processing the measured data, and
c) storing the processed data.

The physical activity of an object, notably a human being, is an important determinant of its health. The amount of daily physical activity is considered to be a central factor in the etiology, prevention and treatment of various diseases. Information about personal physical activity can assist the individual in maintaining or improving his or her functional health status and quality of life.

A system and a method according to the preamble are described in the article "A Triaxial Accelerometer and Portable Data Processing Unit for the Assessment of Daily Physical Activity", by Bouten et al., IEEE Transactions on Biomedical Engineering, Vol. 44, NO. 3, March 1997.

According to the known system and method a triaxial accelerometer composed of three orthogonally mounted uniaxial piezoresistive accelerometers is used to measure accelerations covering the amplitude and frequency ranges of human body acceleration. Thereto an individual wears the triaxial accelerometer over a certain period of time. A data processing unit is attached to the triaxial accelerometer and programmed to determine the time integrals of the moduli of accelerometer output from the three orthogonal measurement directions. These time integrals are summed up and the output is stored in a memory that can be read out by a computer. The output of the triaxial accelerometer bears some relation to energy expenditure due to physical activity and provides as such a measure for the latter.

The known system allows for a complete and accurate measurement of human body acceleration in three directions. Using state of the art techniques in the field of integrated circuit technology the accelerometer can be build small and light weight allowing it to be worn for several days or even longer without imposing a burden to the individual wearing it.

However the known system and method have the disadvantage that the output thereof is in arbitrary units. The outputs of several accelerometers worn by different individuals are thus not comparable in the sense that no quantitative conclusions can be drawn thereon. In fact the same is valid for the outputs of one accelerometer worn by a single individual during different time periods.

It is an object of the invention to provide a system and a method according to the preamble that provides a reproducible and objective measure of the physical activity of an object over a certain period of time.

The system according to the invention is thereto characterized in that it further comprises calculating means for calculating the physical activity level of the object. The method according to the invention is thereto characterized in that it further comprises the step of: d) calculating the physical activity level of the object.

It is known in the relative field that physical activity can be expressed as PAL (Physical Activity Level). PAL is defined as Average Daily Metabolic Rate (ADMR) divided by Basal Metabolic Rate (BMR). The ADMR (or total daily energy expenditure) can be divided into three compartments: BMR, DEE (Diet Induced Energy Expenditure) and AEE (Activity Induced Energy Expenditure). BMR is the amount of energy spent in rest (not asleep) and is strongly correlated with body weight. DEE is the thermogenic effect that occurs after food ingestion and is, for a subject in energy balance, approximately 10% of ADMR. AEE is the amount of energy spent on physical activity and is the most variable of all components and the most difficult to measure. Thus, PAL is a relative and objective number reflecting an individuals activity and is therefore suitable for use in comparison of physical activity between different individuals.

Currently measurements of ADMR are performed by using the known doubly labeled water method. Doubly labeled water ($^2H_2^{18}O$) however is difficult to obtain and expensive. ADMR can also be determined by calculation of heat production from $O_2$ consumption and $CO_2$ production for which purpose an individual has to be confined to a respiration chamber for a period of up to several days. BMR can be determined by calculation of heat production from $O_2$ consumption and $CO_2$ production measured in a respiration chamber or as measured with a ventilated hood. The BMR can also be calculated with known formulas using age, sex, height and weight. Clearly measurement of ADMR and thus PAL is impractical in daily life and certainly not feasible for population studies.

Contrary thereto the invention provides a system and a method to calculate the physical activity level of an individual in a practical manner that can be used in daily life by everyone who is interested in optimizing his health. The system and method according to the invention can for example be used at home for diet adjustment, by a medical professional to improve diagnosis or adjust medication levels in case of diseases, such as coronary diseases or Parkinson's disease, or sleep disorders. The use is certainly not limited to human beings but can be extended to non-living objects, such as buildings or machines, for instance to measure vibrations.

In a first preferred embodiment of the system and the method according to the invention the calculation of the physical activity level of the object is based on the following algorithm:

$$PAL = \text{factor 1} + \text{factor 2}^*(\text{variable 1})^{factor\ 3} + \text{factor 4}^*(\text{variable 2})^{factor\ 5} + \ldots + \text{factor }(2n)^*(\text{variable }n)^{factor(2n+1)}$$

wherein

PAL=physical activity level of the object;

Variable 1 through variable n=variables related to the object and/or the system; and Factor 1 through factor 2n+1=factors to be determined by validation of the system.

According to the first embodiment advantageously all relevant variables relating to the individual object and the system can be accounted for to obtain the physical activity level as an objective measure.

A preferred embodiment is directed to a living subject and the variables related to the subject comprise body mass and/or sleep time and/or age and/or length and/or sex. Preferably the variables related to the system comprise output and/or wear time of the measurement means. The output preferably firstly is processed by the data processing means before being input to the memory means or directly to the calculating means.

From experiments it has been shown that the following algorithm reveals an accurate number for the physical activity level of a living subject:

$$PAL = a + b^*(\text{output})^c + d^*(\text{body mass})^e + f^*(\text{sleep time})^g + h^*(\text{wear time})^i$$

An even more accurate assessment of the physical activity level of the subject can be obtained with the following algorithm:

$$PAL = a + b*(\text{output})^c + d*(\text{body mass})^e + f*(\text{sleep time})^g + h*(\text{wear time})^i + j*(\text{age})^{k+l}*(\text{length})^m + n*(\text{sex})^o$$

According to a preferred embodiment of the system according to the invention the measurement means comprise three orthogonally mounted accelerometers for measuring the acceleration of the object. Measuring the acceleration in vertical, antero-posterior and medio-lateral direction allows for a complete registration of the acceleration of the object.

In another preferred embodiment the accelerometers comprise piezo-electric material allowing the measurement of acceleration without the need for an additional power supply. Preferably the piezo-electric material is uni-axial in order to truly confine the measurement of each accelerometer to one direction. More preferably the piezo-electric material is serial dimorph thus enhancing the sensitivity of the measurements.

In an elegant preferred embodiment the accelerometers have a strip form and are fixed at one end thereof. The mutually orthogonal positioning of the accelerometers can now be realized in a practical way. Furthermore due to this fixation the sensitivity of the accelerometers is relatively high and can be easily enlarged by placing weights at the outer ends of the strips.

In a practical embodiment the system according to the invention comprises an activity monitor in which the measurement means, data processing means and memory means are incorporated, which activity monitor further comprises communication means for communicating with the calculating means. Preferably the calculating means comprise a computer.

The invention also relates to an activity monitor described as part of the above-described system.

The invention also concerns a computer program to carry out one or more of the steps of the method according to the invention.

Figure 2:
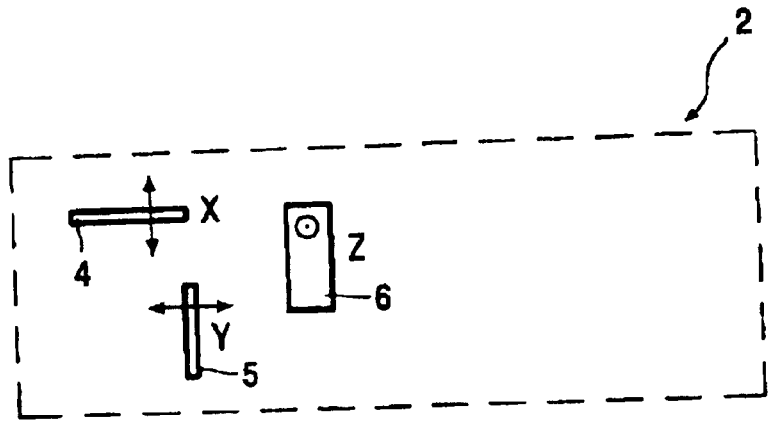
Figure 3:
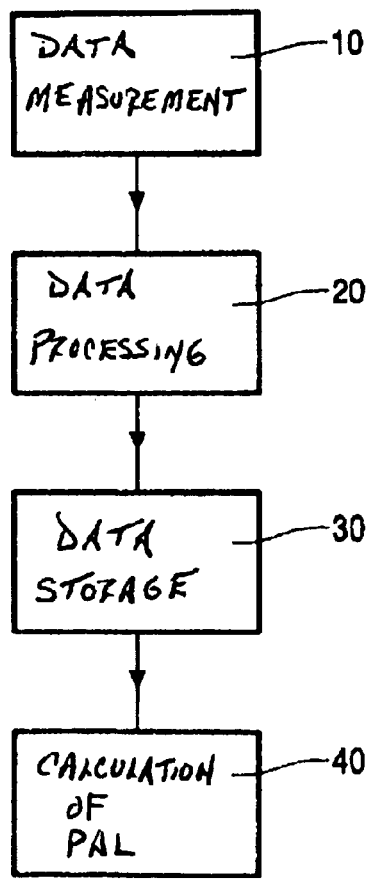

The invention will be further explained by means of the attached drawing, in which:

FIG. 1 shows a block diagram schematically showing the components of the system according to the invention;

FIG. 2 schematically shows the orthogonal position of the three accelerometers of the system according to the invention; and FIG. 3 shows a flow diagram of the steps of the method according to the invention.

FIG. 1 shows the components of system 1, a preferred embodiment of the invention. System 1 comprises an activity monitor 2 that is connectable to calculating means 3. Any suitable calculating means can be selected by a person skilled in the art. In the following the calculating means are formed by a personal computer 3.

The activity monitor 2 is to be attached to the object of which the physical activity level is to be established. For purposes of illustration in the following it is assumed that the object is a human individual. This individual wears the activity monitor 2 for a certain time period.

Three accelerators 4, 5 and 6 are provided to measure the accelerations of the individual's body in three orthogonal directions, known as antero-posterior, medio-lateral and vertical, that are denoted as x, y and z, respectively. The accelerometers comprise strips of piezo-electric material that is uni-axial and serial bimorph. The strips are fixed at one end thereof.

FIG. 2 schematically shows the orthogonal mounting of the accelerators 4, 5 and 6 in which the arrows indicate the direction of freedom of movement.

The piezo-electric accelerators act as damped mass-spring systems, wherein the piezo-electric strips act as spring and damper. Vibrations of the strips due to movement of the individual generate an electric charge leading to a measurement of a data signal. In case of human movements the frequency of the data signals lies in the range of 0,1–20 Hz. The amplitude of the data signals lies between −12 g and +12 g. These numbers are in more detail discussed in the article mentioned earlier as state of the art, which is incorporated herein by reference. Suitable piezo-electric materials to measure such data signals are known to a person skilled in the art.

The data signals coming from accelerators 4, 5 and 6 are fed to a data processing unit 7 for separate processing. The processing unit separately integrates data signals of each accelerator over a certain time period, e.g. one minute. The result is stored as one data point. The data processing unit 7 is powered by a battery 9 and a DC/DC converter 11.

Said data points are stored in memory 8, which is preferably a flash memory preserving the stored data after a malfunction in the power supply. Preferably the storage capacity is sufficient to retain data measured during a period of several weeks.

At the end of the time period the data points are summed and averaged over time yielding an output in counts/unit time.

The data processing unit 7 is further connected to communication means 12 for communicating with the calculating means, in this example computer 3. Communication means 12 may comprise an RS 232 port.

In this respect it is noted that the calculating means do not necessarily have to be provided separately from the activity monitor, but can optionally be integrated therein. The preferred embodiment shown and described herein does have the advantage that it can be made lightweight and small. The importance of these features however depends on the intended use of the system.

Computer 3 serves two main purposes. Firstly it calculates the physical activity level of the individual based on the data points. Secondly it may be used to program the data processing unit 7.

In system 1 several different activity monitors 2 can communicate with computer 3. Thereto each activity monitor is assigned a unique code that is made available at the start of each communication session.

The calculation of the physical activity level (PAL) is performed according to the method according to the invention. The most important steps of that method are mentioned in the flow diagram of FIG. 3. Each step is discussed in more detail below.

Step 10 Data Measurement

In step 1 data signals relating to the movement of an object under examination, in this example a human individual, are measured. Preferably data signals are measured in three dimensions, since this provides the most accurate results. According to a preferred embodiment the data signals are measured with the system shown in FIGS. 1 and 2 and described above. Thereto the individual wears the activity monitor 2 for a certain time period, usually a couple of days.

In this description the system and method of the invention are described However, it must be noted that there are several other commercially available systems for measuring a persons movements, which are suitable for use in stead of the activity monitor 2 for performing the method according to the invention.

Step 20 Data Processing

The data signals of each measurement direction measured in step 1 are separately processed. Preferably the data signals measured in one direction are integrated over a certain time period, such as one minute. The result of such an integration is referred to as a data point.

Step 30 Data Storage

The data points resulting from the processing in step 2 are stored in memory. Preferably the data points are stored separately for each direction.

In order to improve the accuracy of the measurements means are provided to correct the measurements afterwards. Thereto a correction factor is stored in memory, which is to be applied to the data points.

Step 40 Calculation of PAL

Based on the data points the physical activity level (PAL) of the individual is calculated. Thereto the following algorithm is defined:

$$PAL = \text{factor } 1 + \text{factor } 2*(\text{variable } 1)^{factor\ 3} + \text{factor } 4*(\text{variable } 2)^{factor\ 5} + \ldots + \text{factor } (2n)*(\text{variable } n)^{factor(2n+1)}$$

Variable 1 through variable n are variables related to the object and/or the system. In the current example where the object is a human individual the variables related to the subject may for instance comprise body mass and/or sleep time and/or age and/or length and/or sex. The variables related to the system may comprise output and/or wear time of the measurement means. The output preferably firstly is processed by the data processing means before being input to the memory means or directly to the calculating means. In this example the output comes from the activity monitor, which incorporates both measurement means and the data processing means.

According to a first preferred embodiment the following algorithm is used:

$$PAL = a + b*(\text{output})^c + d*(\text{body mass})^e + f*(\text{sleep time})^g + h*(\text{wear time})^i$$

According to a second preferred embodiment the algorithm is extended to:

$$PAL = a + b*(\text{output})^c + d*(\text{body mass})^e + f*(\text{sleep time})^g + h*(\text{wear time})^i + j*(\text{age})^k + l*(\text{length})^m + n*(\text{sex})^o$$

Factor 1 through factor 2n+1 are factors, preferably constants, the value of which is to be determined by validation of the system.

Validation Step

When the formula is defined by choice of the variables of interest as described above, the factors have to be determined in a validation step. This step only has to be performed once, during a validation period, after which the thus validated algorithm is ready for use.

As noted above PAL is defined as ADMR/BMR. For purposes of validation ADMR and BMR first have to be established in order to define a validation value of PAL that is denoted as $PAL_{val}$. ADMR can for instance be measured with the doubly labeled water method, which is considered the golden standard in measuring energy expenditure in daily life, or by means of indirect calorimetry in a respiration chamber. The latter method (if deired with a ventilated hood instead of a respiration chamber) can be used to objectively measure BMR. Alternatively BMR can also be calculated by methods known in the field. With this information $PAL_{val}$ can now be calculated.

During the validation period the individual under examination has to wear the activity monitor, or any other suitable measurement means, in order to collect relevant movement data.

At the end of the validation period all variables determined in the validation step can be filled-in in the selected formula yielding the missing values for the factors.

It is noted that ADMR and BMR can be determined by any suitable method or by any device that is validated for energy expenditure. It is for instance conceivable that a system according to the invention after validation is used for determination of $PAL_{val}$ in the validation of another system.

After the validation step the algorithm is ready for use. An individual wears the activity monitor 2 over a self-selected period of time. At the end of said period the output of the activity monitor is communicated to the calculating means 3 for calculation of the PAL. The value of PAL is an objective value that can be compared with own previous values or with reference values. As is known in the field the value of PAL for a human individual generally ranges between the minimum of 1,0 and a maximum of approximately 2,5 for an extremely active subject. Values higher than 2,5 are sometimes reached by professional endurance athletes.

Now the method of the invention is explained a skilled person will be able to translate the steps 20, 30 and 40 of the method into a computer program to carry out the method.

Summarizing the invention teaches a system and a method for calculating the physical activity level of an object as an objective measure for the physical activity of that object. The calculation is based on the movements of that object.

For purposes of illustration of the invention only the object's acceleration is measured by means of accelerators forming part of an activity monitor described herein. The invention is however not limited to the use of such an activity monitor nor to the use of acceleration data to represent the object's movements. Contrary thereto many commercially available devices, such as other accelerometers, pedometers or any kind of physical activity meters, for measuring an object's movements are suitable as an alternative for the activity monitor described herein. Such a device can supply the data relating to the movement of the object to any kind of suitable calculating means for calculating the physical activity level according to the invention.

The invention is of course not limited to the described or shown embodiment, but generally extends to any embodiment, which falls within the scope of the appended claims as seen in light of the foregoing description and drawings.

What is claimed is:

1. System (1) for determining a measure of the physical activity of an object over a certain period of time, said system comprising measurement means (4,5,6) for measuring data relating to movement of the object, data processing means (7) for processing the measured data and memory means (8) for storing the processed data, characterized in that, the system further comprises calculating means (3) for calculating the physical activity level of the object, wherein the calculating means are arranged to calculate the physical activity level of the object based on the following algorithm:

$$PAL = \text{factor } 1 + \text{factor } 2*(\text{variable } 1)^{factor\ 3} + \text{factor } 4*(\text{variable } 2)^{factor\ 5} + \ldots + \text{factor } (2n)*(\text{variable } n)^{factor\ (2n+1)}$$

wherein

PAL=physical activity level of the object;

Variable 1 through variable n=variables related to the object and/or the system; and Factor 1 through factor 2n+1=factors to be determined by validation of the system.

2. The system according to claim 1, wherein the object is a living subject and the variables related to the subject comprise body mass and/or sleep time and/or age and/or length and/or sex.

3. The system according to claim 1, wherein the variables related to the system comprise wear time of the measurement means and/or output of the measurement means, data processing means or memory means.

4. The system according to claim 1, wherein the object is a living subject and the calculating means are arranged to calculate the physical activity level of the subject based on the following algorithm:

$$PAL=a+b*(\text{output})^c+d*(\text{body mass})^e+f*(\text{sleep time})^g+h*(\text{wear time})^i.$$

5. The system according to claim 1, wherein, the object is a living subject and the calculating means are arranged to calculate the physical activity level of the subject based on the following algorithm:

$$PAL=a+b*(\text{output})^c+d*(\text{body mass})^e+f*(\text{sleep time})^g+h*(\text{wear time})^i+j*(\text{age})^{k+l}*(\text{length})^m+n*(\text{sex})^o.$$

6. The system according to claim 1, comprising an activity monitor (2) in which the measurement means, data processing means and memory means are incorporated, which activity monitor further comprises communication means (12) for communicating with the calculating means.

7. The system according to claim 1, wherein the calculating means comprise a computer.

8. Activity monitor described as part of the system according to claim 1.

9. The system according to claim 1, wherein the measurement means comprise three orthogonally mounted accelerometers for measuring the acceleration of the object.

10. The system according to claim 9, wherein the accelerometers have a strip form and are fixed at one end thereof.

11. The system according to claim 9, wherein the accelerometers comprise piezo-electric material.

12. The system according to claim 11, wherein the piezo-electric material is uni-axial.

13. The system according to claim 11, wherein the piezo-electric material is serial bimorph.

14. A method for determining a measure of the physical activity of an object over a certain period of time comprising the acts of:

a) measuring data relating to movement of the object;

b) processing the measured data;

c) storing the processed data; and a) calculating the physical activity level of the object, based on the following algorithm:

$$PAL=\text{factor 1}+\text{factor 2}*(\text{variable 1})^{\text{factor 3}}+\text{factor 4}*(\text{variable 2})^{\text{factor 5}}+\ldots+\text{factor }(2n)*(\text{variable }n)^{\text{factor }(2n+1)}$$

wherein

PAL=physical activity level of the object;

Variable 1 through variable n=variables related to the object and/or the system; and Factor 1 through factor 2n+1=factors to be determined by validation of the system.

15. The method according to claim 14, wherein the object is a living subject and the variables related to the subject comprise body mass and/or sleep time and/or age and/or length and/or sex.

16. The method according to claim 14, wherein the variables related to the system comprise wear time of the measurement means and/or output of the measurement means, data processing means or memory means.

17. The method according to claim 14, wherein the object is a living subject and the act of calculating the physical activity level of the subject is based on the following algorithm:

$$PAL=a+b*(\text{output})^c+d*(\text{body mass})^e+f*(\text{sleep time})^g+h*(\text{wear time})^i.$$

18. The method according to claim 14, wherein the object is a living subject and the act of calculating the physical activity level of the subject is based on the following algorithm:

$$PAL=a+b*(\text{output})^c+d*(\text{body mass})^e+f*(\text{sleep time})^g+h*(\text{wear time})^i+j*(\text{age})^{k+l}*(\text{length})^m+n*(\text{sex})^o.$$

19. Computer program to carry out one or more of the steps of the method according to claim 14.

* * * * *